United States Patent [19]
Perryman

[11] Patent Number: 6,072,144
[45] Date of Patent: Jun. 6, 2000

[54] APPARATUS FOR MEASURING THE QUALITY OF SPOT WELDS

[75] Inventor: Raymond Andrew George Perryman, Moulton, United Kingdom

[73] Assignee: Graphers Systems Limited, United Kingdom

[21] Appl. No.: 08/933,653

[22] Filed: Sep. 19, 1997

[30] Foreign Application Priority Data

Sep. 27, 1996 [GB] United Kingdom .................... 9620229

[51] Int. Cl.[7] ................................................ B23K 11/25
[52] U.S. Cl. ............................................ 219/109; 228/104
[58] Field of Search ................................. 219/109, 110; 228/104; 73/628, 641, 644

[56] References Cited

U.S. PATENT DOCUMENTS

| | | | |
|---|---|---|---|
| 3,384,733 | 5/1968 | Burbank et al. | 219/109 |
| 4,208,917 | 6/1980 | Aoyama et al. | 73/644 |
| 4,530,362 | 7/1985 | Hetz | 73/628 |
| 5,280,724 | 1/1994 | Higo et al. | 73/628 |
| 5,644,085 | 7/1997 | Lorraine et al. | 73/641 |
| 5,677,490 | 10/1997 | Gunther et al. | 73/628 |

FOREIGN PATENT DOCUMENTS

| | | |
|---|---|---|
| 715143 | 9/1954 | United Kingdom . |
| 774675 | 5/1957 | United Kingdom . |
| 2015159 | 9/1979 | United Kingdom . |

*Primary Examiner*—Clifford C. Shaw
*Attorney, Agent, or Firm*—Nields, Lemack & Dingman; Brian M. Dingman

[57] ABSTRACT

Apparatus (2) for measuring the quality of spot welds, comprising a housing (4); a fluid medium (6) in the housing (4); transmitter means (8) for transmitting at least one ultrasonic pulse through the fluid medium (6) to a spot weld (10), the ultrasonic pulse then reverberating in the spot weld (10); and receiver means (16) through which the ultrasonic pulse passes on its way to the spot weld (10), the receiver means (16) being ultrasonically sensitive so that it is able to receive echoes from the spot weld (10) by the reverberation of the ultrasonic pulse in the spot weld (10), the receiver means (16) comprising a plurality of ultrasonically sensitive elements (18), and the receiver means (16) being such that during use of the apparatus (2) the receiver means (16) is located adjacent the spot weld (10).

11 Claims, 9 Drawing Sheets

6,072,144

APPARATUS FOR MEASURING THE QUALITY OF SPOT WELDS

This invention relates to apparatus for measuring the quality of spot welds.

There are three different known ways of measuring the quality of spot welds. The first way is a destructive way which involves ripping open the weld to expose the spot weld for measurement with a vernier or gauge. The second way is semi-destructive and it involves using a chisel to prise apart two welded parts in order to reach the edge of the weld with a gauge. The third way is a non-destructive way which involves using an ultrasonic probe which is manipulated by an operator whilst the operator interpretes an ultrasonic echo pattern received from the spot weld.

The testing of spot welds is essential in the vehicle manufacturing industry since the strength of a vehicle body and therefore its safety is governed by the strength of the spot welds, that is resistance spot welds. There are also many other instances where spot welds are used and where their quality needs to be measured. The above mentioned methods of testing involving ripping open the weld or prising apart welded parts self-evidently cause damage to the product under test and this damage is self-evidently disadvantageous. The above mentioned ultrasonic test is not accurate and it requires the use of skilled operators.

It is an aim of the present invention to provide apparatus for measuring the quality of spot welds, which apparatus uses ultrasonics so that it is non-destructive, and which apparatus is able to provide more accurate measurements in a simpler manner than the known ultrasonic apparatus.

Accordingly, the present invention provides apparatus for measuring the quality of spot welds, which apparatus comprises a housing; a fluid medium in the housing; transmitter means for transmitting at least one ultrasonic pulse through the fluid medium to a spot weld, the ultrasonic pulse then reverberating in the spot weld; and receiver means; the receiver means being ultrasonically sensitive so that it is able to receive echoes from the spot weld caused by the reverberation of the ultrasonic pulse in the spot weld, the receiver means being positioned in the vicinity of a bottom part of the housing so that the ultrasonic pulse passes through the receiver means on its way to the spot weld and so that the receiver means is able to be pressed directly over the spot weld in plan view, the receiver means comprising a plurality of ultrasonically sensitive elements, and the ultrasonically sensitive elements being small in relation to the size of the receiver means and the spot weld so that an echo is able to be collected from each ultrasonically sensitive element that is nearest an echo source in the spot weld before the echoes from adjacent ultrasonically sensitive elements interfere with each other, whereby the apparatus is able to obtain the equivalent of an accurate contact print of the spot weld.

The apparatus of the present invention may measure the quality of the spot welds by measuring their size. The use of the receiver means with the plurality of ultrasonically sensitive elements enables precise measurement readings to be obtained by unskilled operators.

Preferably, the transmitter means is a piezoelectric transmitter means. Other types of transmitter means may however be employed.

The ultrasonically sensitive elements in the receiver means may be in the form of lines for giving a line scan of the spot weld. Alternatively, the ultrasonically sensitive elements in the receiver means may be in the form of an array for totally covering an area of the spot weld.

Preferably, the receiver means is a piezoelectric receiver means with the ultrasonically sensitive elements being piezoelectric ultrasonically sensitive elements. The piezoelectric receiver means is preferably in the form of a film. The film is preferably a piezoelectric polyvinylidene fluoride film.

Other types of receiver means may be employed so that, for example, the receiver means may be any suitable and appropriate ultrasonically sensitive receiver means such for example as a piezo-resistive ultrasonically resistive receiver means.

The housing is preferably in the form of a tube. Other shapes for the housing may however be employed. By having the housing in the form of a tube, the apparatus is able to be manufactured in the form of a probe for easy location on the spot weld.

The fluid medium is preferably water but other materials may be employed providing they are suitable and appropriate for use with the ultrasonic pulse. Thus, for example, the fluid medium may be oil or a water-based ultrasonic couplant. The fluid medium acts as a delay line and the slow ultrasonic pulse velocity of water makes water especially suitable for use in the apparatus of the present invention.

Usually, the apparatus of the invention will include signal processing means for processing signals received from the receiver means. Thus, for example, the signal processing means may process all the signals received from a particular measurement from a spot weld, in order to log and/or give a print out or display of the characteristics of the weld.

Embodiments of the invention will now be described solely by way of example and with reference to the accompanying drawings in which.

Figure 1:
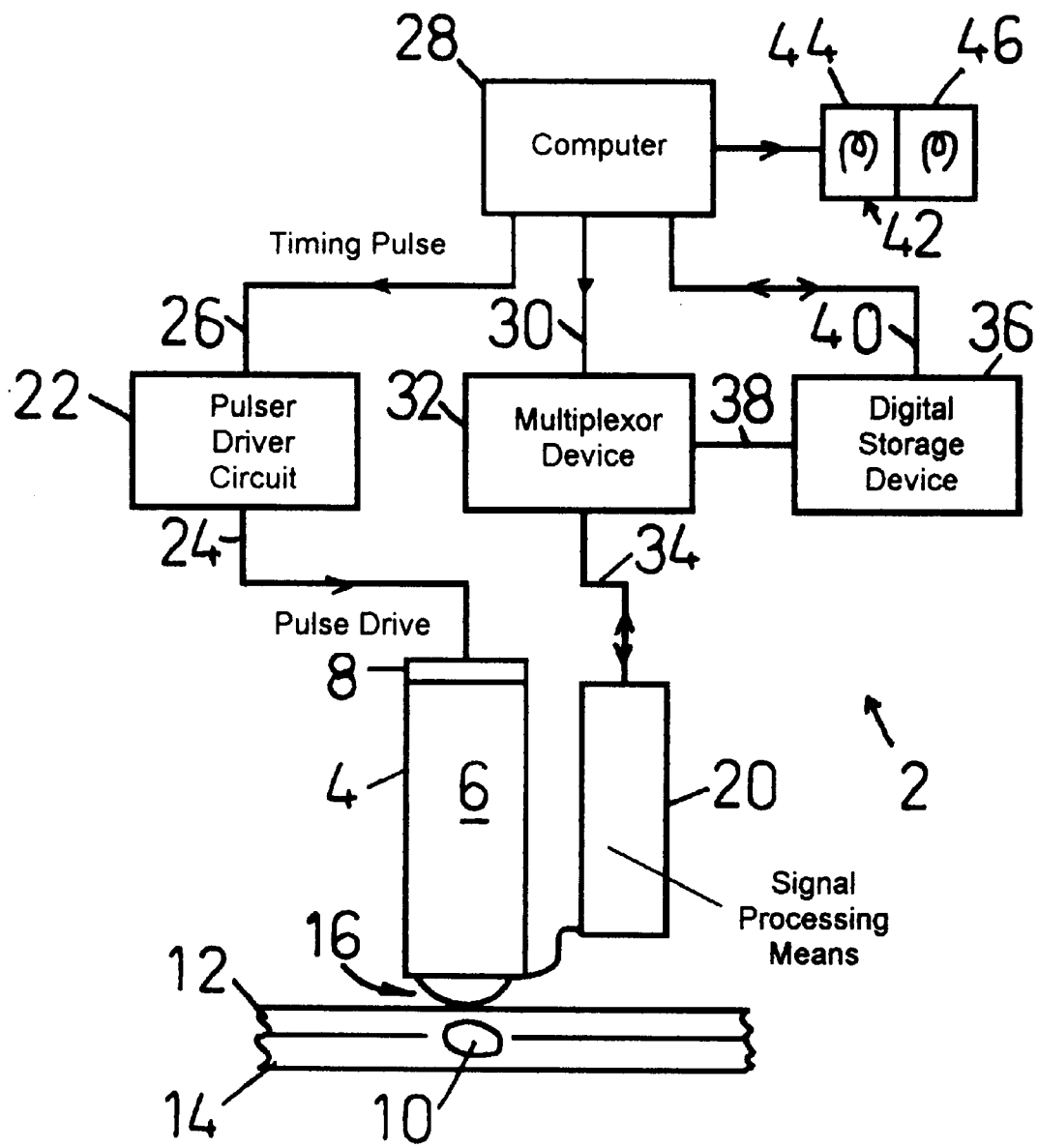
FIG. 1 is a schematic layout of apparatus for measuring the quality of spot welds.

Referring to FIG. 1, there is shown apparatus 2 for measuring the quality of spot welds. The apparatus 2 comprises a housing 4 which contains a fluid medium 6 in the form of water. The housing 4 also contains transmitter means 8 for transmitting an ultrasonic pulse through the fluid medium 6 to a spot weld 10. The spot weld 10 is shown welding together two panels 12, 14 forming part of the body for a car or other vehicle. The ultrasonic pulse reverberates in the spot weld 10 when it engages the spot weld 10.

The apparatus 2 further comprises receiver means 16. The receiver means 16 is positioned at the bottom of the housing 4 so that the ultrasonic pulse passes through the receiver means 16 on its way to the spot weld 10. The receiver means 16 is ultrasonically sensitive so that it is able to receive echoes from the spot weld 10 caused by the reverberations of the ultrasonic pulse in the spot weld 10.

Figure 4:
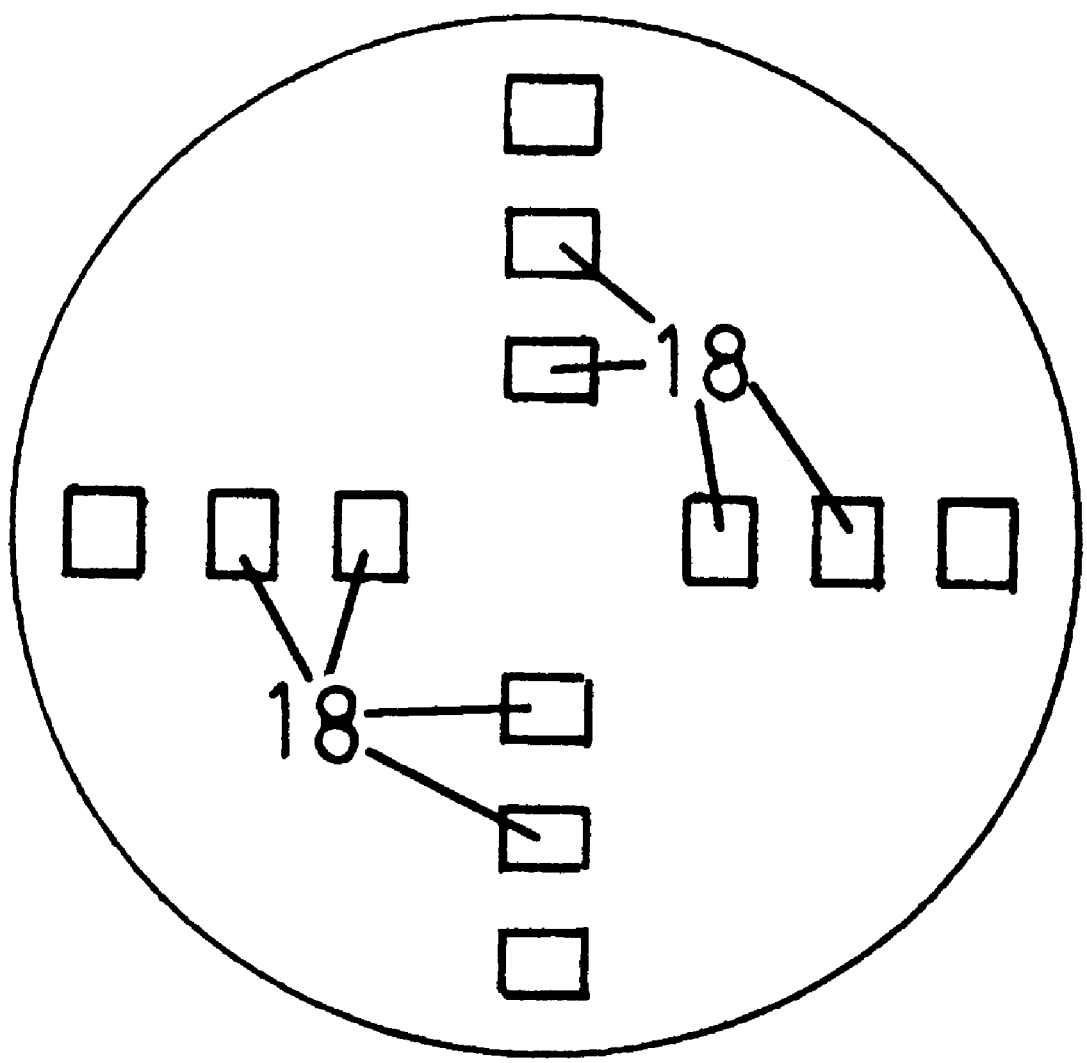
FIG. 4 shows one form of layout for ultrasonically sensitive elements forming part of receiver means.

The receiver means 16 comprises a plurality of ultrasonically sensitive elements 18 which, as shown in FIG. 4, are arranged in the form of a cross. This gives line scanning of the spot weld 10. As will be appreciated from FIG. 2, the receiver means 16 is such that during use of the apparatus 2, the receiver means 16 is located adjacent the spot weld 10.

The transmitter means 8 is a piezoelectric transmitter means 8.

The receiver means 16 is a piezoelectric receiver means with the ultrasonically sensitive elements 18 being piezoelectric ultrasonically sensitive elements 18. As can best be appreciated from FIG. 2, the piezoelectric receiver means 16 is in the form of a film. The film is a piezoelectric polyvinylidene fluoride film.

Figure 2:
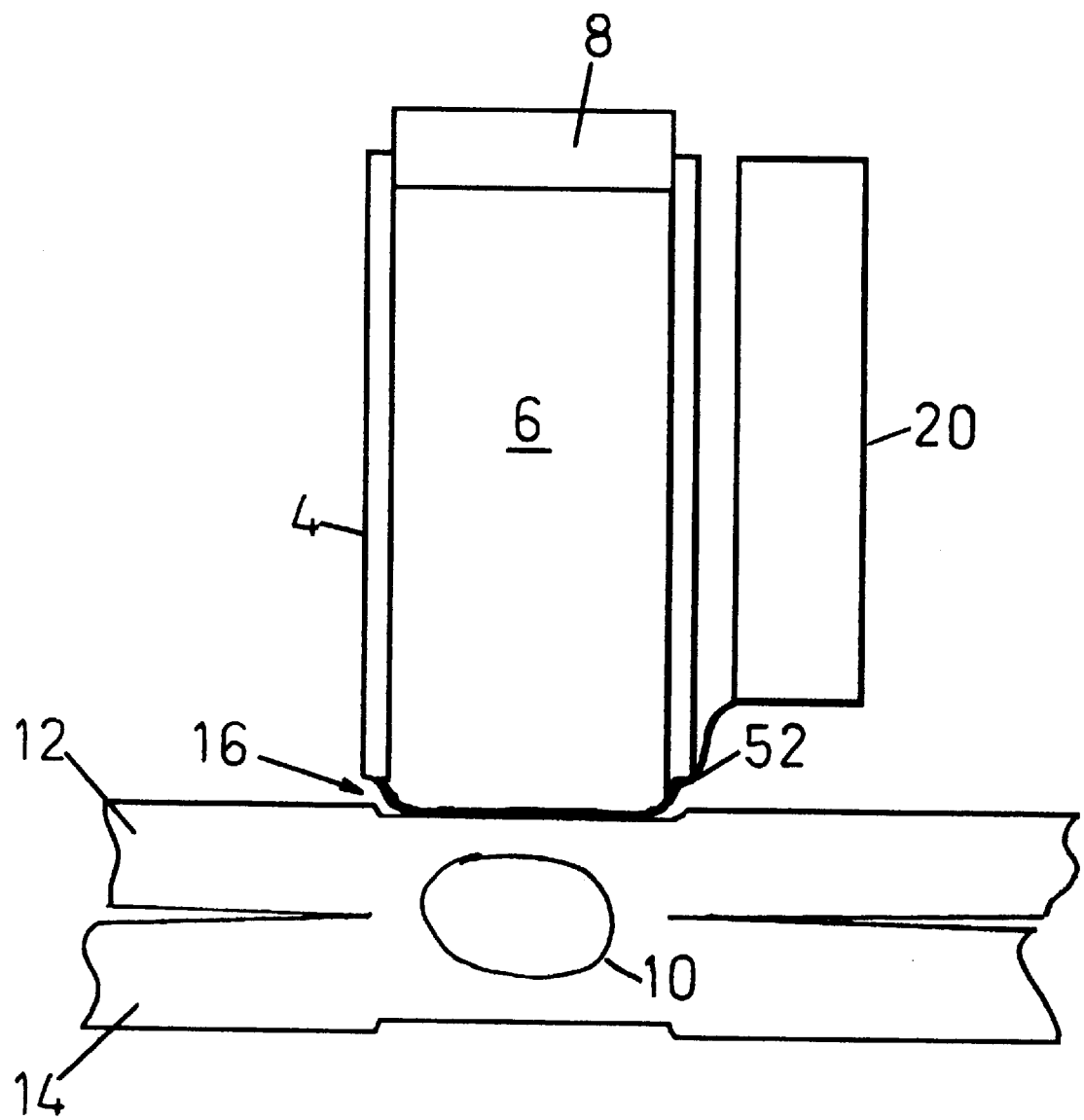
FIG. 2 is an enlarged view of part of the apparatus shown in FIG. 1.

As can be seen from FIGS. 1 and 2, the housing 4 is in the form of a tube. The housing 4 can thus easily be held in the nature of a probe for easy positioning over the spot weld 10.

As shown in FIG. 1, the apparatus 2 includes signal processing means 20 for processing signals received from the receiver means 16. Also as shown in FIG. 1, the apparatus 2 comprises a pulse driver circuit 22 for providing a pulse drive along line 24 for the transmitter means 8. A timing pulse for the pulse driver circuit 22 is provided along line 26 from a computer 28. The computer 28 processes data as appropriate. The computer 28 provides address signals along line 30 to a multiplexer device 32 which in turn is connected by line 34 to the data processing means 20. A digital storage device 36 is connected by line 38 to the multiplexer device 32, and by line 40 to the computer 28. The digital storage device 36 may give fast transient capture of signals obtained in the signal processing means 20.

The computer 28 may have a visual display unit 42 having a red light 44 and a green light 46. The red light 44 will become illuminated if the spot weld 10 being measured is not up to standard. The green light 46 will be illuminated if the spot weld 10 being measured is up to standard. The lights 44, 46 may be provided external to the computer 28 or they may be provided on a screen of the computer 28. The screen of the computer 28 may also display a weld summary or image.

Figure 3:
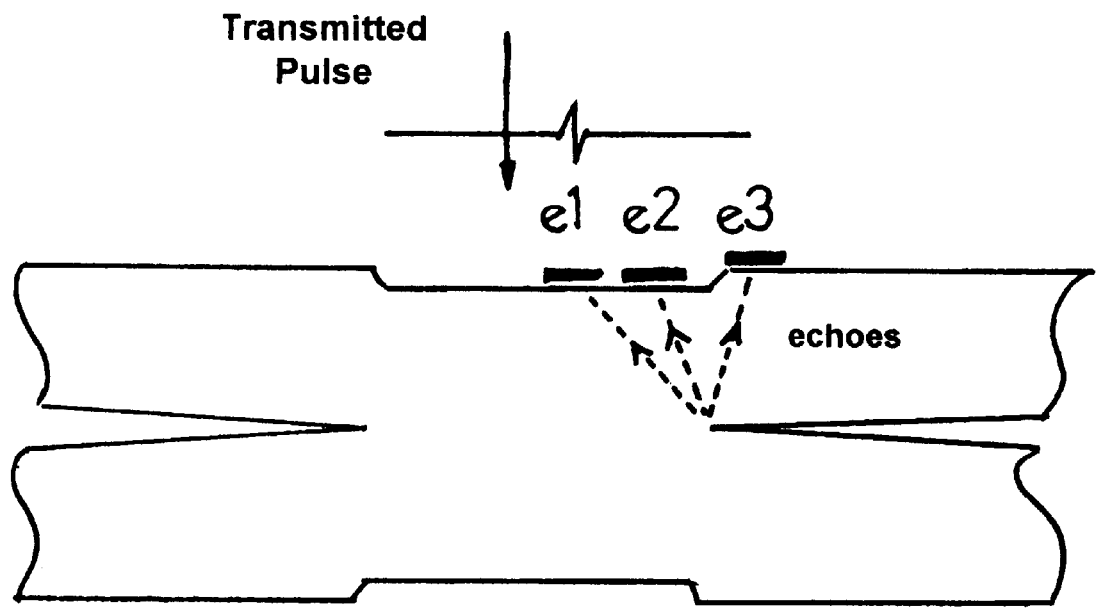
FIG. 3 illustrates how echo data is processed.
Figure 3:
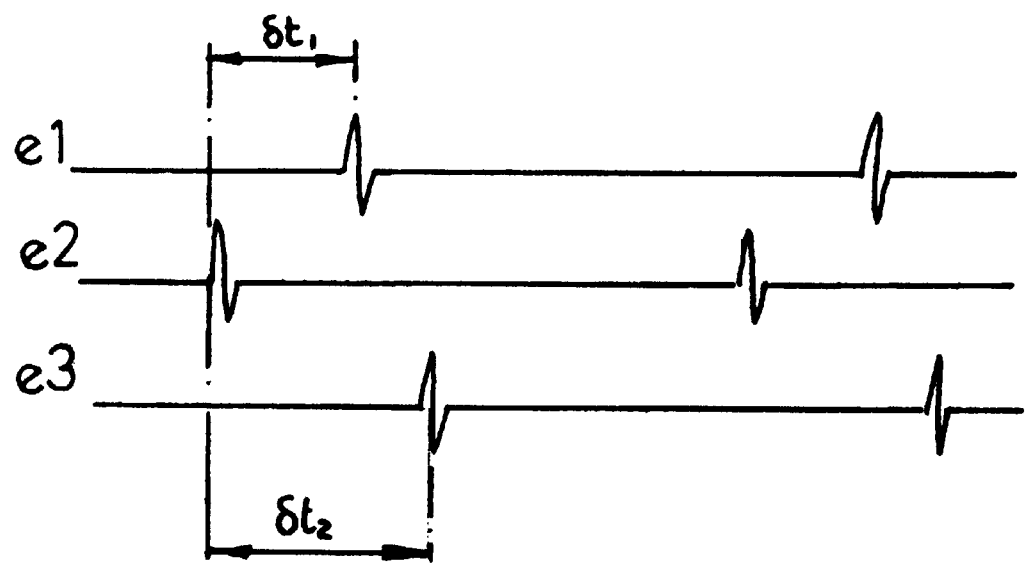

During operation of the apparatus 2, when the ultrasonic pulse strikes the spot weld 10, it reverberates in the spot weld 10 and echoes are caused. These echoes are shown in FIG. 3 as E1, E2 and E3. The ultrasonically sensitive elements 18 pick up these echoes E1, E2 and E3 at different times. The echo signals are processed together, for example, one thickness delay at a given particular angle. This reduces noise and increases signal strength.

Figure 5:
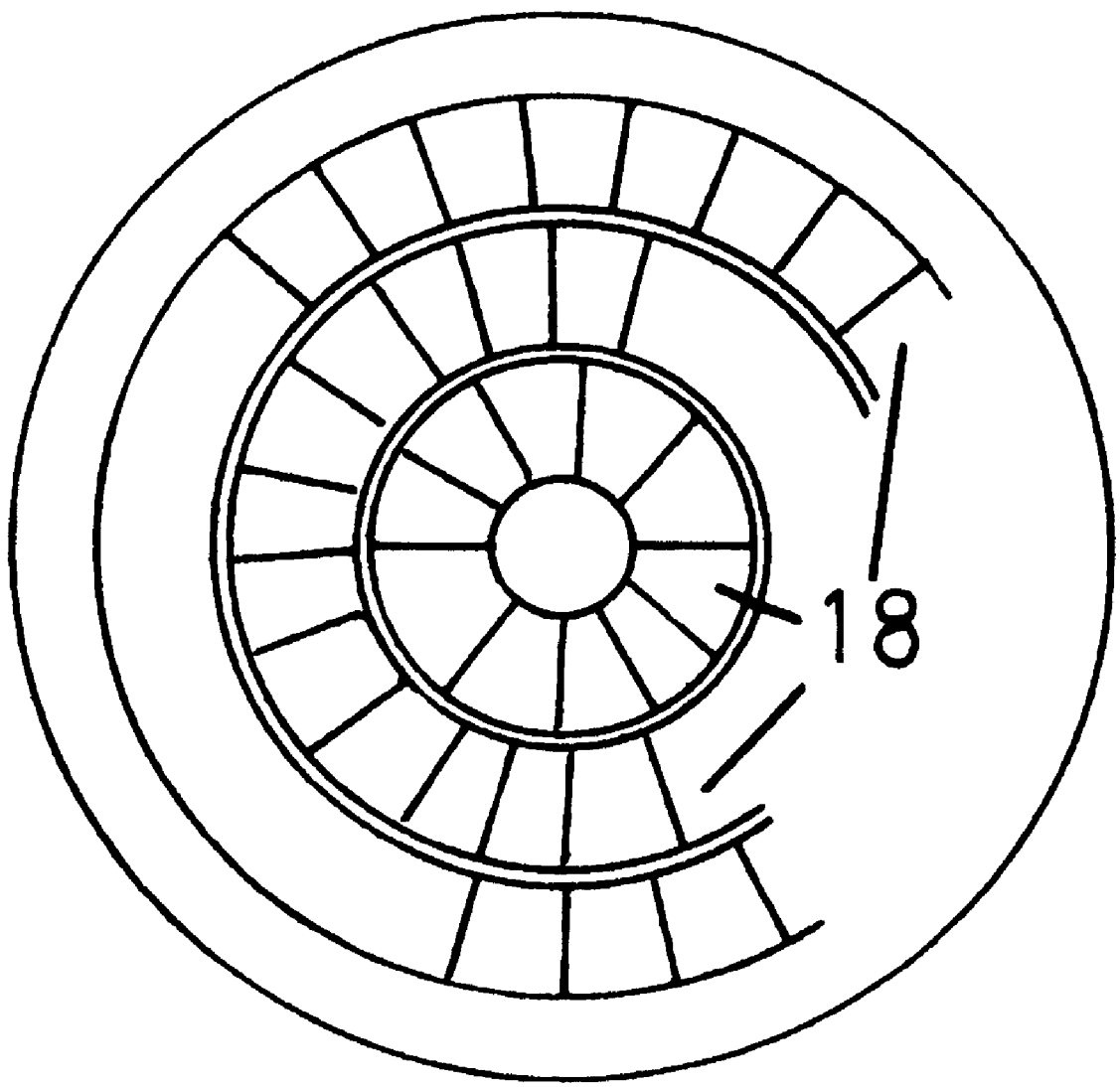
FIG. 5 shows an alternative layout to that shown in FIG. 4 for the ultrasonically sensitive elements forming part of the receiver means.

FIG. 5 shows an alternative arrangement of the ultrasonically sensitive elements 18. As can be seen, the ultrasonically sensitive elements 18 are in the form of a circular array for totally covering an area of the spot weld 10.

Figure 6:
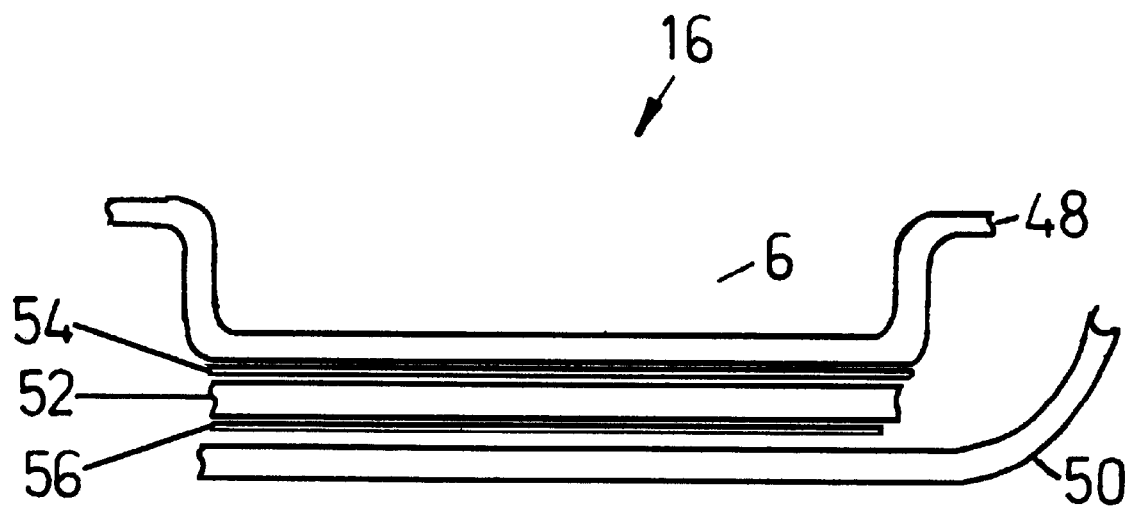
FIG. 6 is an enlarged cross section through part of the receiver means shown in FIG. 2.

Referring now to FIG. 6, there is shown a cross section through the receiver means 16. It will be seen that the receiver means 16 comprises two flexible circuit boards 48, 50 separated by a polyvinylidene fluoride film 52. The flexible circuit boards 48, 50 and the film 52 have electrodes as appropriate. The flexible circuit boards 48, 50 and the film 52 are held together by two layers of conductive adhesive tape 54, 56 as shown. The flexible circuit board 48 forms a seal for the polymer fluid material 6 in the housing 4. The flexible circuit board 50 forms a wear surface for contacting the spot weld 10. As shown in FIG. 2, the film 52 is connected to the signal processing means 20.

Figure 7:
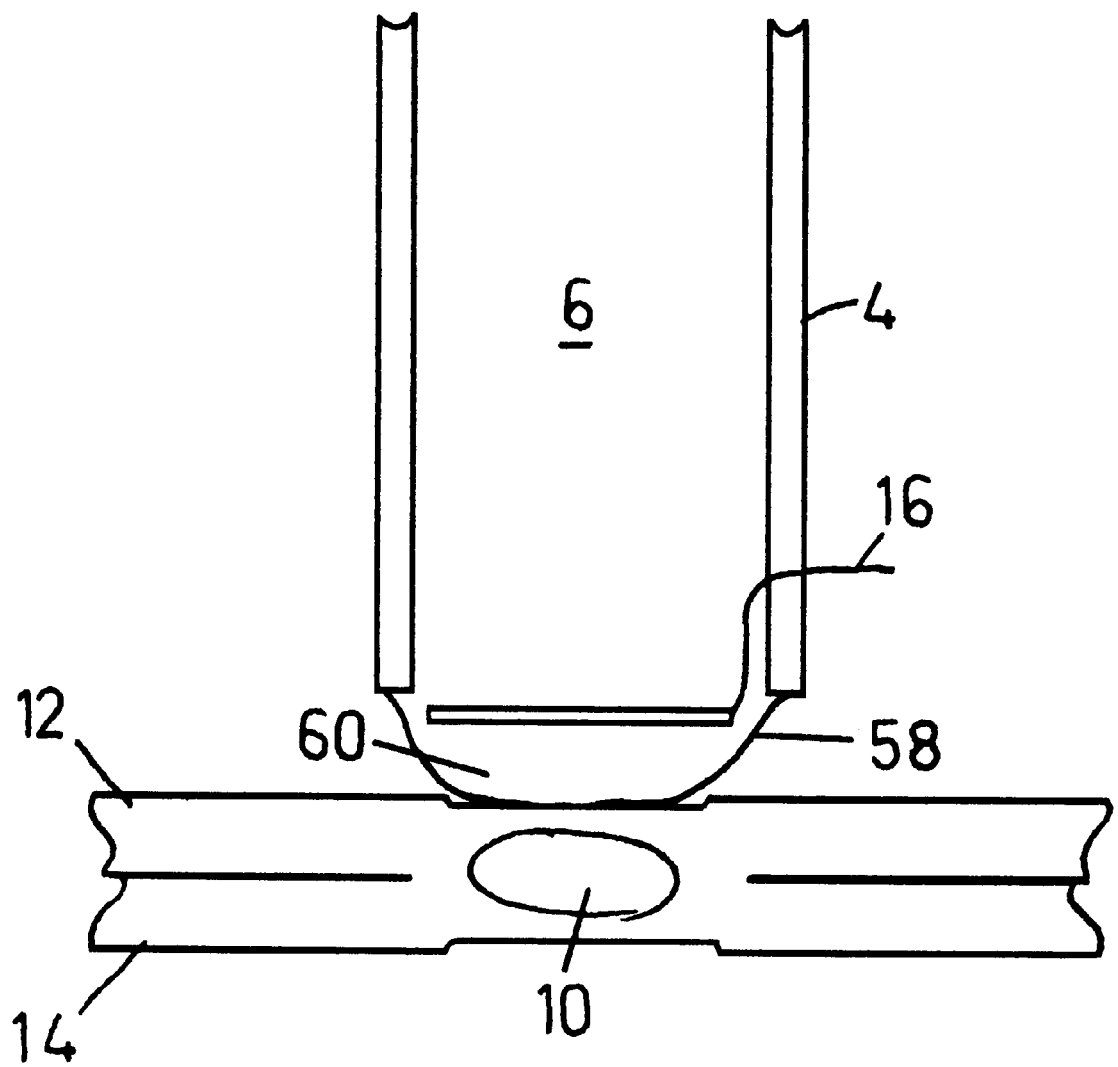
FIG. 7 shows an alternative part of the apparatus to that shown in FIG. 2.

Referring now to FIG. 7, there is shown an alternative arrangement to that shown in FIG. 2. Similar parts as in FIG. 2 have been given the same reference numerals for ease of comparison and understanding. In FIG. 7, the receiver means 16 is spaced apart from the bottom of the housing 4 which is formed by a water sealing device 58. A space 60 between the receiver means 16 and the water sealing device 58 may be filled with a coupling material.

Figure 8:
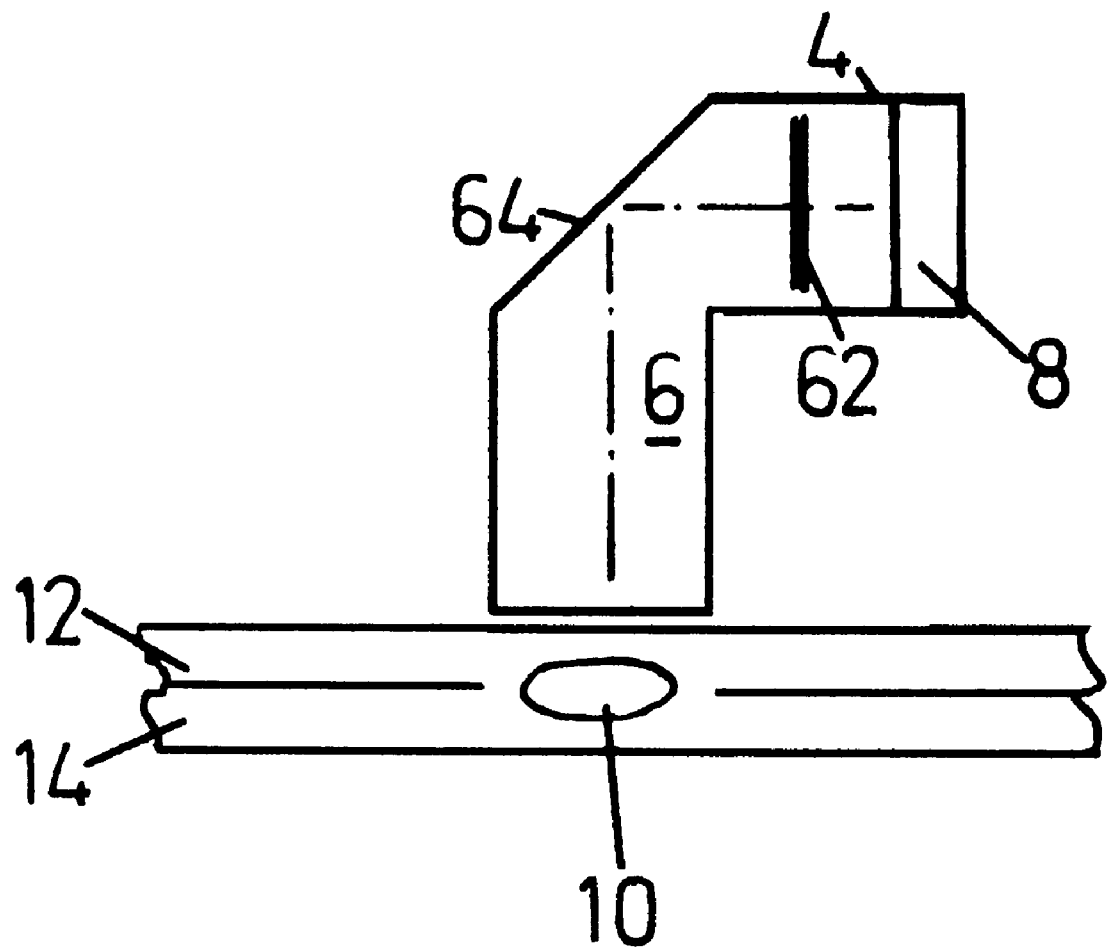
FIG. 8 shows another construction for the apparatus to that shown in FIG. 2.
Figure 9:
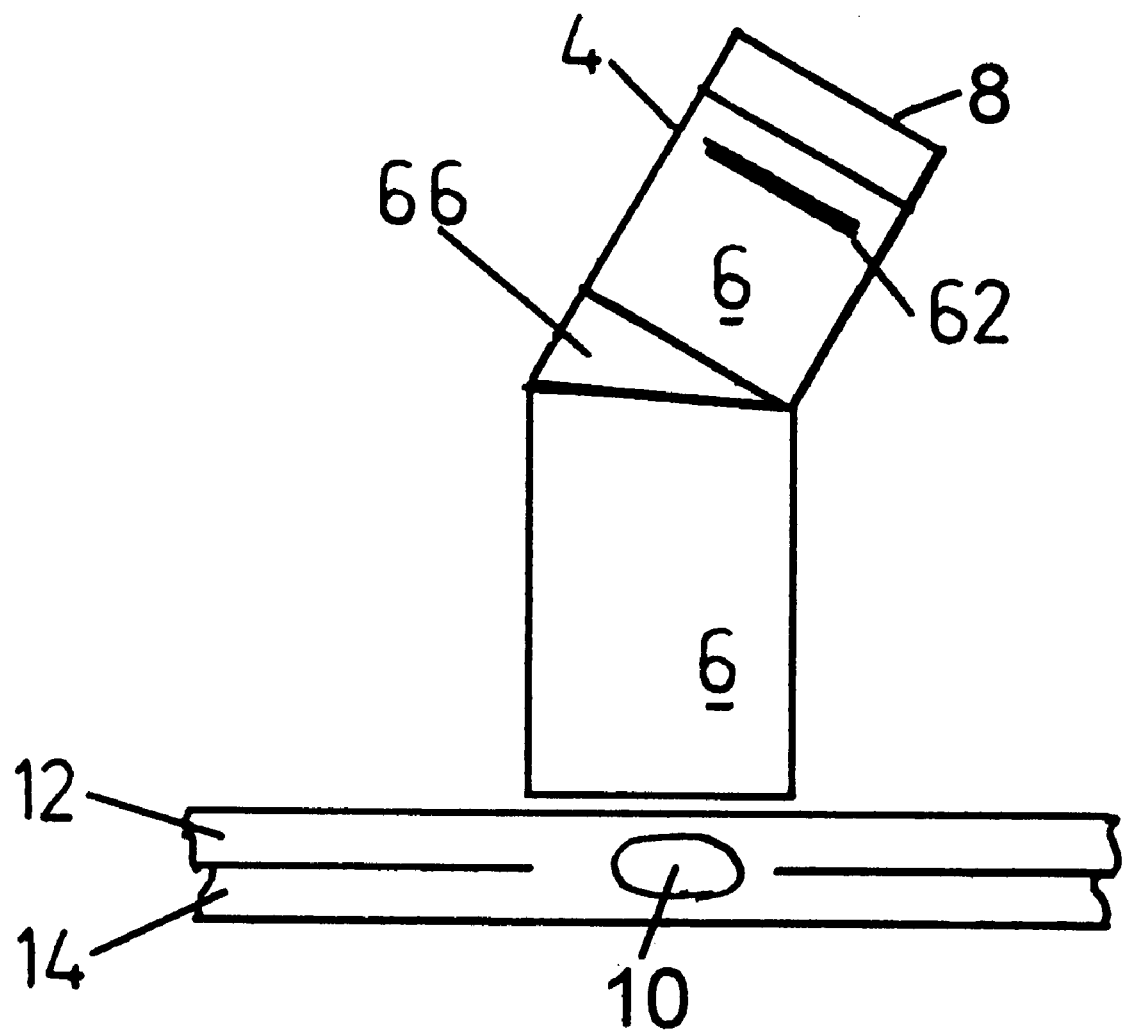
FIG. 9 shows a yet further alternative construction for the apparatus shown in FIG. 2.

FIGS. 8 and 9 show two different designs for the housing 4. In FIG. 8 the single transmitted pulse from the transmitter 8 is shown as pulse 62 which is reflected by a reflector 64 through, for example, 90°. In FIG. 9, a refractive material 66 is employed to bend the pulse 62 as shown. The refractive material may be, for example, perspex.

The apparatus 2 shown in the drawings is such that the receiver means 16 is able to be placed on top of the spot weld 10 to receive the ultrasonic echoes. This allows an ultrasonic contact print of the spot weld 10 to be captured and enhanced using appropriate software in the signal processing means 20. The receiver means 16 and the software allow a point of focus to be slid over the spot weld 10, looking down into the spot weld 10 in order to find the edges of the spot weld 10 and its size. This has benefits because the apparatus 2 is able to detect the effects caused by different small features in the spot weld 10 because the apparatus 2 does not average the echoes as in the known ultrasonic apparatus. Still further, the apparatus of the present invention is less sensitive to the angle of the housing 4 to the weld than in the known ultrasonic apparatus, because the receiver means 16 is right on top of the spot weld 10 whereas in the known ultrasonic apparatus, the receiver means is at the end of a housing remote from the spot weld 10. With the apparatus 2 of the present invention, there is no need to move the housing.

During operation of the apparatus 2, an interrogating pulse is transmitted from the transmitter means 8. The pulse enables the gathering of information from a particular pad in the receiver means 16. The pulse passes through the receiver means 16 and into the spot weld 10. The echoes passed back through the receiver means 16 and into the column of the fluid means 6. As the ultrasonic echoes pass through the receiver means 16, the receiver means 16 catches the signals and processes them to enable a measurement of the weld to be obtained. The collected data from each ultrasonically sensitive element 18 in the receiver means 16 comes from each ultrasonic sensitive element 18 that is nearest an echo source in the spot weld 10. The receiver means 16 is thus able to make an extremely accurate contact print of the spot weld 10. Each ultrasonically sensitive element 18 is small and it is able to pick up ultrasonic signals equally strongly from a wide angle. If it is desired to enhance the contact print, wide angle viewing can be narrowed using software employing a method such for example as a synthetic aperture focusing technique as the angle narrowing method.

The initial measurements are for measuring the diameter of the spot weld 10. Furthermore subtle measurements that may be effected are measurements to find solidification cracks, the "stuck" zone (a weak brazed ring can form with coated steels), weld nugget volume, or the nature of the structure within the spot weld 10.

It is to be appreciated that the embodiments of the invention described above with reference to the accompanying drawings have been given by way of example only and that modifications may be effected. Thus, for example, the film 52 is preferably 50 um thick but other thicknesses may be employed. Similarly, the flexible circuit boards 48, 50 are preferably 25 um thick but other thicknesses may be employed. The flexible circuit boards 48, 50 are preferably made of a nylon material but other materials may be employed. Contact pads for the flexible circuit boards 48, 50 and the film 52 may be provided by sputter coating depositing aluminium on the film, or by etching aluminium electrodes from an aluminized surface layer.

If desired, a single ultrasonic pulse may be used to interrogate the spot weld, with each pad being separately measured as a signal in response to the single pulse. However, this would require expensive equipment capable of very fast multiplexing, capture and storage, or it would require a capture and storage channel for each pad. Less expensive equipment involves the use of one digital capture system with at least one pulse for each pad to be measured. To make a complete measurement, a set of pulses will be used. In sequence, the computer will change the address to connect each pad, via the multiplexer to the scope. To capture each pad's signal and improve the signal to noise ratio, it may be desirable to average the pad signal by taking, for example, 16 pulses per pad.

What is claimed is:

1. Apparatus for measuring the quality of spot welds, which apparatus comprises a housing; a fluid medium in the housing; transmitter means for transmitting at least one ultrasonic pulse through the fluid medium to a spot weld, the ultrasonic pulse then reverberating in the spot weld; and receiver means; the receiver means being ultrasonically sensitive so that it is able to receive echoes from the spot weld caused by the reverberation of the ultrasonic pulse in the spot weld, the receiver means being positioned in the vicinity of a bottom part of the housing so that the ultrasonic pulse passes through the receiver means on its way to the spot weld and so that the receiver means is able to be pressed directly over the spot weld in plan view, the receiver means comprising a plurality of ultrasonically sensitive elements, and the ultrasonically sensitive elements being small in relation to the size of the receiver means and the spot welt so that an echo is able to be collected from each ultrasonically sensitive element that is nearest an echo source in the spot weld before the echoes from adjacent ultrasonically sensitive elements interfere with each other, whereby the apparatus is able to obtain the equivalent of an accurate contact print of the spot weld.

2. Apparatus according to claim 1 in which the transmitter means is a piezoelectric transmitter means.

3. Apparatus according to claim 1 in which the ultrasonically sensitive elements in the receiver means are in lines for giving a line scan of the spot weld.

4. Apparatus according to claim 1 in which the ultrasonically sensitive elements in the receiver means are in an array for covering an area of the spot weld.

5. Apparatus according to claim 1 in which the receiver means is a piezoelectric receiver means with the ultrasonic sensitive elements being piezoelectric ultrasonically sensitive elements.

6. Apparatus according to claim 5 in which the piezoelectric receiver means is in the form of a film.

7. Apparatus according to claim 6 in which the piezoelectric receiver means is a piezoelectric polyvinylidene fluoride film.

8. Apparatus according to claim 1 in which the housing is in the form of a tube.

9. Apparatus according to claim 1 in which the fluid medium is water.

10. Apparatus according to claim 1 and including signal processing means for processing signals received from the receiver means.

11. Apparatus for measuring the quality of spot welds, which apparatus comprises a housing; a fluid medium in the housing; transmitter means for transmitting at least one ultrasonic pulse through the fluid medium to a spot weld, the ultrasonic pulse then reverberating in the spot weld; and receiver means; the receiver means being ultrasonically sensitive so that it is able to receive echoes from the spot weld caused by the reverberation of the ultrasonic pulse in the spot weld, the receiver means being positioned in the vicinity of a bottom part of the housing so that the ultrasonic pulse passes through the receiver means on its way to the spot weld and so that the receiver means is able to be pressed directly over the spot weld in plan view, the receiver means comprising a plurality of ultrasonically sensitive elements, the ultrasonically sensitive elements being small in relation to the size of the receiver means and the spot weld so that an echo is able to be collected from each ultrasonically sensitive element that is nearest an echo source in the spot weld before the echoes from adjacent ultrasonically sensitive elements interfere with each other, whereby the apparatus is able to obtain the equivalent of an accurate contact print of the spot weld, and the apparatus being one in which the receiver means is a piezoelectric receiver means with the ultrasonically sensitive elements being piezoelectric ultrasonically sensitive elements, in which the piezoelectric receiver means is in the form of a film, in which the piezoelectric receiver means is a piezoelectric polyvinylidene fluoride film, and in which the housing is in the form of a tube for being held in a person's hand during use of the apparatus.

* * * * *